US010705719B2

(12) United States Patent
Jakowitz

(10) Patent No.: US 10,705,719 B2
(45) Date of Patent: Jul. 7, 2020

(54) OPERATING SYSTEM FOR OPERATING A MULTIFUNCTION SYSTEM

(71) Applicant: Harman Becker Automotive Systems GmbH, Karlsbad (DE)

(72) Inventor: Tino Jakowitz, Karlsbad (DE)

(73) Assignee: Harman Becker Automotive Systems GmbH, Karlsbad (DE)

(*) Notice: Subject to any disclaimer, the term of this patent is extended or adjusted under 35 U.S.C. 154(b) by 317 days.

(21) Appl. No.: 15/786,951

(22) Filed: Oct. 18, 2017

(65) Prior Publication Data

US 2018/0113592 A1 Apr. 26, 2018

(30) Foreign Application Priority Data

Oct. 21, 2016 (DE) .................. 10 2016 120 075

(51) Int. Cl.
*G06F 3/0484* (2013.01)
*G06F 3/0488* (2013.01)
(Continued)

(52) U.S. Cl.
CPC .............. *G06F 3/0488* (2013.01); *A61F 4/00* (2013.01); *G01C 21/3664* (2013.01);
(Continued)

(58) Field of Classification Search
CPC .......... G06F 3/00; G06F 3/041; G06F 3/0412; G06F 3/0414; G06F 3/0428; G06F 3/048;
(Continued)

(56) References Cited

U.S. PATENT DOCUMENTS 4,218,603 A 8/1980 Satoh
6,963,762 B2 11/2005 Kaaresoja et al.
(Continued)

FOREIGN PATENT DOCUMENTS

DE 102012102749 A1 10/2013
DE 102013013168 A1 2/2015
(Continued)

OTHER PUBLICATIONS

Pangaro, G., et al., "Actuated Workbench", 2002, website: http://tangible.media.mit.edu/project/actuated-workbench/ accessed Nov. 13, 2019, 1 pg.

*Primary Examiner* — Xiomara L Bautista
(74) *Attorney, Agent, or Firm* — Brooks Kushman P.C.

(57) ABSTRACT

An operating system for operating a multifunction system that operates in a blind mode of operation and in a visual mode of operation. The operating system includes a touch-sensitive screen that displays a plurality of virtual function elements for controlling different functions. In the blind mode of operation, the virtual function elements are actuated without viewing the screen, and, in the visual mode of operation, the virtual function elements are activated while viewing the screen. A guide element and an additional operation element are connected to the screen. A control unit controls at least the guide element and the additional operating element provides, in the blind mode of operation, perceivable or audible feedback based on an actuation of the screen if a body part of the operator contacts the screen with one of the virtual function elements.

20 Claims, 9 Drawing Sheets

(51) Int. Cl.
*A61F 4/00* (2006.01)
*G09B 21/00* (2006.01)
*G06F 3/01* (2006.01)
*G06F 3/0481* (2013.01)
*G06F 3/16* (2006.01)
*G06F 3/0482* (2013.01)
*G01C 21/36* (2006.01)
*G06F 9/48* (2006.01)

(52) U.S. Cl.
CPC .............. *G06F 3/013* (2013.01); *G06F 3/016* (2013.01); *G06F 3/0482* (2013.01); *G06F 3/04817* (2013.01); *G06F 3/04842* (2013.01); *G06F 3/162* (2013.01); *G06F 3/167* (2013.01); *G06F 9/4843* (2013.01); *G09B 21/00* (2013.01); *G06F 2203/04809* (2013.01)

(58) Field of Classification Search
CPC .. G06F 3/0481; G06F 3/04817; G06F 3/0482; G06F 3/0484; G06F 3/04842; G06F 3/0487; G06F 3/0488; G06F 3/16; G06F 3/162; G06F 3/167; G06F 16/00; G06F 16/60; G06F 16/63; G06F 9/48; G06F 9/4843
See application file for complete search history.

(56) References Cited

U.S. PATENT DOCUMENTS

| | | | |
|---|---|---|---|
| 2010/0084249 | A1 | 4/2010 | Bandy et al. |
| 2011/0310049 | A1* | 12/2011 | Homma ............... G06F 3/04883 345/173 |
| 2012/0300061 | A1* | 11/2012 | Osman .................. G06F 1/3231 348/135 |
| 2013/0342501 | A1 | 12/2013 | Molne et al. |
| 2014/0215340 | A1* | 7/2014 | Shetty ................... G06F 3/0488 715/727 |
| 2015/0029089 | A1* | 1/2015 | Kim ........................ G06F 3/011 345/156 |
| 2015/0160772 | A1* | 6/2015 | Takeuchi .............. G06F 3/0414 345/177 |
| 2018/0376055 | A1* | 12/2018 | Kondo ............... H04N 5/23293 |

FOREIGN PATENT DOCUMENTS

| | | |
|---|---|---|
| DE | 102013015204 A1 | 3/2015 |
| DE | 102014019159 A1 | 6/2016 |
| WO | 2014047674 A1 | 4/2014 |

* cited by examiner

OPERATING SYSTEM FOR OPERATING A MULTIFUNCTION SYSTEM

CROSS-REFERENCE TO RELATED APPLICATIONS

This application claims foreign priority benefits under 35 U.S.C. § 119(a)-(d) to DE Application Serial No. 10 2016 120 075.1, filed Oct. 21, 2016, the disclosure of which is hereby incorporated in its entirety by reference herein.

TECHNICAL FIELD

The present invention relates to an operating system for operating a multifunction system, which is configured to be operated in a blind mode of operation and in a visual mode of operation.

BACKGROUND

In the past, multifunction systems, particularly in a vehicle environment, have been provided with several actuation elements, particularly in a vehicle environment, in order to activate and control the different functions of the multifunction system. Due to the arrangement of the individual actuation elements relative to one another, an operator, knowing the multifunction system with the individual actuation elements, was able to operate the actuation elements almost blindly by feeling the shape and the position of the actuation elements. Touch-sensitive screens are now also beginning to be used in the vehicle environment. These touch-sensitive screens are used to control the different functions in the vehicle environment, wherein, due to the representation of virtual function elements on the screen, it is possible to activate the assigned function if a virtual function element is actuated by the operator. In a vehicle environment, in the case of a driver, it is important that the attention of the operator is not diverted excessively from the traffic events, so that the multifunction system should be operated without directing the gaze onto the screen on which the virtual function elements are displayed. However, with a conventional touch-sensitive screen, this is not possible, since, depending on the operating mode selected, the screen has different arrangements of the virtual function elements, and the function elements cannot be felt. However, when viewing the touch-sensitive screen, it should preferably also be possible to select the virtual function elements unchanged to the extent possible, if the operator looks at the screen and activates the associated function by simply pressing a virtual function element.

Therefore, an aim of the present invention is to avoid the above disadvantages and to provide a system which can be operated without the operator having to view the screen, wherein, at the same time, in a visual mode of operation, if the operator is viewing the screen, the virtual function elements can be activated more or less unchanged.

SUMMARY

This aim is achieved by the features of the independent claim. In the dependent claims, additional embodiments are described.

According to a first aspect, an operating system for operating a multifunction system is provided. The operating system is configured to be operated in a blind mode of operation and in a visual mode of operation. The operating system comprises a touch-sensitive screen which is configured to display several virtual function elements for controlling different functions of the multifunction system. In a blind mode of operation, an operator actuates the virtual function elements without viewing the screen, while, in the visual mode of operation, the operator actuates the virtual function elements while viewing the screen. The system comprises a guide element which is in connection with the screen, and an additional operating element which is in connection with the screen. Moreover, the operating system comprises a control device which is configured to control at least the guide element and the additional operating element, and which, in the blind mode of operation, in the case of actuation of the screen, provides perceivable or audible feedback if a body part of the operator comes in contact on the screen with one of the virtual function elements. If the control unit detects that the body part of the operator comes to lie on this virtual function element, and a first predetermined actuation of this particular virtual function element by the body part is present, nonvisual information on the particular virtual function element is made available to the operator. In the case of actuation of this particular virtual function element, the control unit is configured to activate a function stored in the particular virtual function element, through the additional operating element with a second predetermined actuation.

With the guide element and the movement of the guide element over the screen, the operator can obtain nonvisual information on the virtual function element, for example, as to which function the virtual operating element, on which the guide element lies, is controlling at a given time. The additional operating element can then be used to activate the function associated with the virtual function element. Thereby, the operating system can also be operated in a blind mode of operation. The operator does not have to look at the screen to learn which function is stored on a virtual function element or icon; this can be explained to the operator by nonvisual information such as via an audio output.

Moreover, it is possible that the control device can distinguish whether the operating system is in the blind mode of operation or in the visual mode of operation.

If the operating system recognizes that it is operated in the visual mode of operation, the activation of the individual functions can occur directly, as is conventional in the case of a touch-sensitive screen, by touching the associated virtual function element on the screen. In the blind mode of operation, the function is actuated by the above-mentioned second predetermined actuation. Preferably, the control device is here configured so that, in the visual mode of operation, it does not to enable the activation of the function stored in the particular virtual function element, by the operation of the additional operating element with the second predetermined actuation. This means that, for the activation of a function of a virtual function element in the visual mode of operation, a different actuation than in the blind mode of operation is necessary. In the visual mode of operation, a function can be selected immediately, for example, by touching the respective virtual function element, while, in the blind mode of operation, this actuation does not select the functions.

The above-explained features and additional features described below can be used not only with the corresponding explicitly represented combinations but also in other combinations or separately, without leaving the scope of protection of the present invention.

The above-described properties, features and advantages of the invention as well as the manner in which they are achieved become clearer and more understandable in con-

DETAILED DESCRIPTION

Figure 1:
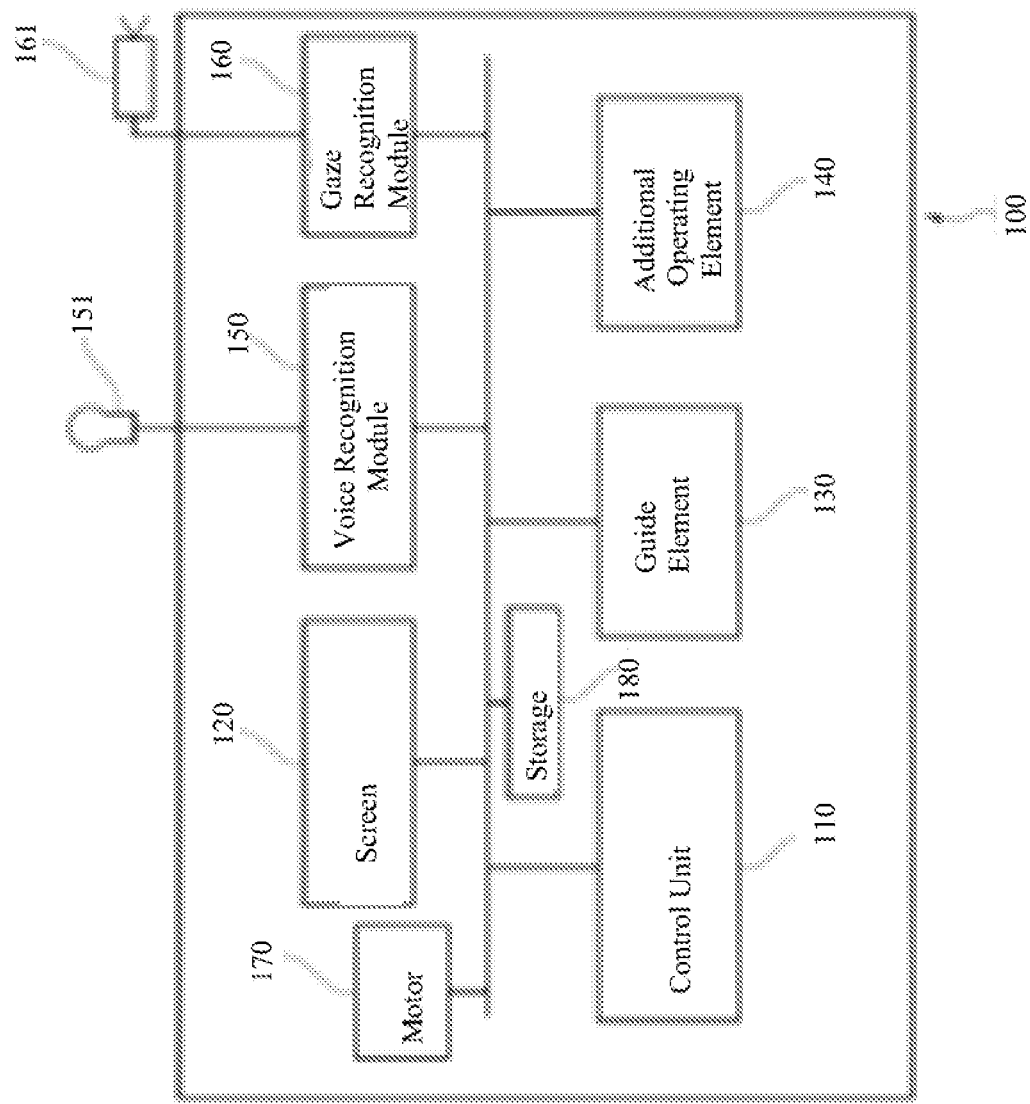
FIG. 1 diagrammatically shows an operating system which can be operated in the blind mode of operation and in the visual mode of operation.

Below, the present invention is explained in further detail using preferred embodiments in reference to the drawings. In the figures, identical reference numerals mark identical or similar elements. The figures are diagrammatic representations of different embodiments. Elements represented in the figures are not necessarily represented true to scale. Rather, the different elements represented in the figures are reproduced in such a manner that their function and purpose are understandable to the person skilled in the art. Connections and couplings between functional units and elements represented in the figures can also be implemented as an indirect connection or a coupling. A connection or coupling can be implemented by wire connection or wirelessly. Functional units can be implemented as hardware, software, or a combination of hardware and software.

FIG. 1 diagrammatically shows an operating system 100 which can be actuated in a blind mode of operation and in a visual mode of operation. The system 100 can be arranged in a motor vehicle or in another environment, in which an operator of the system 100 is to operate the system without having to view the screen 120 present in the system 100, where virtual function elements are arranged for the activation of different functions. The system 100 comprises the touch-sensitive screen 120 as well as a guide element 130. The guide element 130 is used for guiding on the screen 120 in the blind mode of operation. As explained later, the guide element can be a haptic actuation element or it can be configured as a vibration motor, such as the motor 170, which causes either the screen or another element to vibrate if a body part of the operator such as a finger, for example, is moved over the screen in order to explore which virtual function element is represented where, without looking at the screen. The motor 170 is configured in such a manner that either the screen itself vibrates or a mechanical actuation element present on the screen vibrates, as is also explained in detail below. Optionally, the system 100 can also comprise a voice recognition module 150 with a microphone 151. This voice recognition module 160 is capable of detecting and recognizing voice commands of the operator, wherein these commands are then converted by the system 100. Moreover, optionally a gaze recognition module 160 is provided with a camera 161. This gaze recognition module is capable of recognizing the gaze direction and the focus of the operator, and, in particular, it is able to recognize whether the operator is viewing the screen 120 or has it in the vision field or not. Moreover, an additional operating element 140 is provided, in which, in the blind mode of operation, a function of a virtual function element can be called up. A control unit 110 is configured to control the manner of functioning of the system 100, as is also explained in detail below. Moreover, a storage unit 180 is provided, which can store software, for example. The control unit 110 can comprise one or more processors, and the instructions stored in a storage unit 180 can be processed by the processor unit, which is not shown, in the control unit 110, in order to enable the functionality of the operating system 100 which is also explained below in detail.

The system 100 may also comprise additional hardware elements or functional elements, not shown, but which are not explained for clarity.

The system 100 represented in FIG. 1 can be operated in a blind mode of operation. In this case, the operator, for example, the driver of a vehicle, operates the system 100 without looking at the screen 120. The operator can thus concentrate on other things such as, for example, the surrounding traffic. However, in order to provide the operator with feedback as to what the operator or body part of the operator is touching on the screen 120 at a given moment, the system 100 can generate audible or perceivable feedback. In the blind mode of operation, an exploratory mode can be activated, in that nonvisual information is made available to the operator, as to which function is carried out when a certain virtual function element is activated. In this exploratory mode, the operator can find the location on the screen 120 on which the associated virtual function element is represented without looking at the screen 120. One question which, for example, is answered by this exploratory mode, is the following question:

"Where is the function element for changing or raising the interior temperature or the seat temperature?" This exploratory mode can be activated, for example, if the operator remains for a specified first-time span (for example, for 2 seconds) on a function element and touches the function element.

Moreover, in the blind mode of operation, an explanatory mode is possible. This explanatory mode is used for explaining the entire system. For example, in the explanatory mode, the virtual function elements which can be seen just then on the screen 120 can be explained to the operator. In addition to the exploratory mode, an explanation can be provided here as to which use and functionality the individual virtual operating elements have. A possible question here may be the following question:

"How can I raise the temperature in the interior of the vehicle or the seat temperature?" This explanatory mode can be activated, for example, when the operator stays on the function element for a fixed second time span that is longer than the first-time span.

Figure 2:
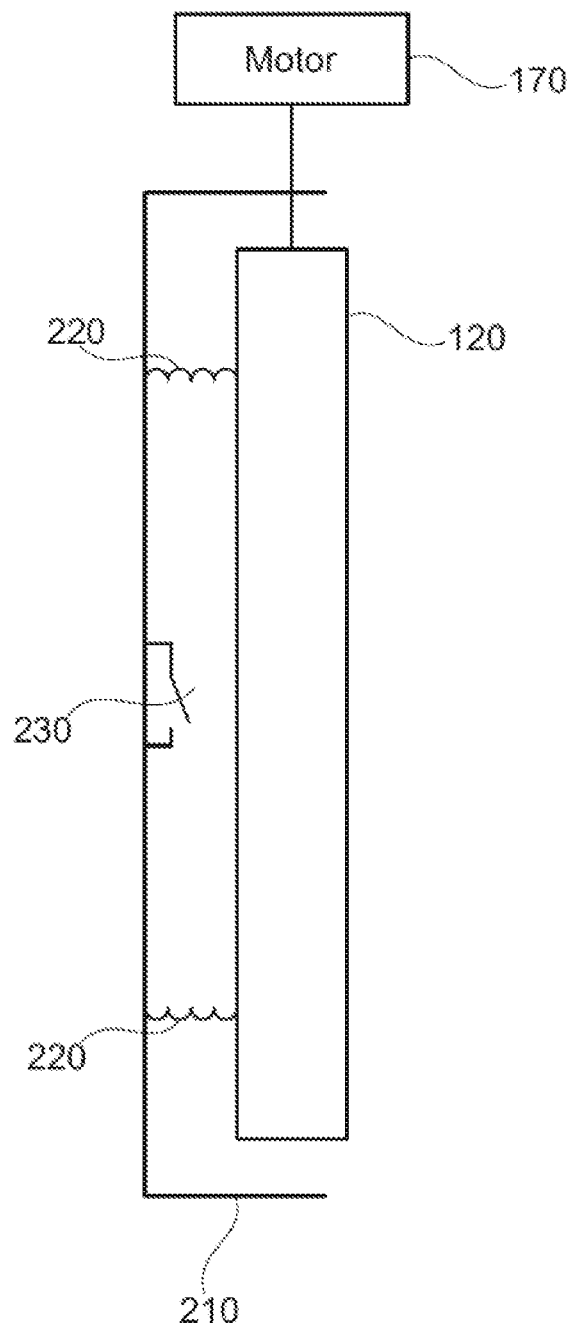
FIG. 2 diagrammatically shows a side view in which a section of the operating system in a first embodiment is represented.

Below, different embodiments are described. In FIG. 2, an embodiment is shown, in which the touch-sensitive screen 120 is mounted by spring elements 220 movably in a holder

210. Moreover, a switch 230 is provided, which has the function of the additional operating element in this embodiment. This switch 230 is used in order to be able to distinguish whether the operator in the exploratory mode would only like to obtain information on a virtual function element or whether the associated function is to be activated. The switch 230 is actuated only if the entire screen 120 is pressed against the spring elements in the direction of the switch 230. Due to the fit of the screen 120 and of the frame 210, the pressing in of the screen 120 always occurs at the same time on the entire surface, so that the screen 120 is moved parallel to the resting position of FIG. 2 in the direction of the switch 230. A function of a virtual operating element is here actuated only if the operator touches the associated function element on the screen 120, and, at the same time, the screen 120 is pushed backward so that the switch 230 is actuated. In this case, an execution of the function can occur only if the switch 230 is actuated and the associated function element is touched. As a result, it is possible to distinguish whether an operator is moving a body part, i.e., a finger, only in an exploratory mode over the screen 120, in order to obtain, for example, audio information on the virtual function element that the finger is touching. Moreover, the motor 170 is represented diagrammatically, in which the screen 120 can be set to vibrate to give feedback to the operator if the operator passes over the surface or an edge of a virtual function element.

In this embodiment, it is possible that the system by itself does not recognize whether it is actuated in the blind mode of operation or the visual mode of operation. Instead, the system assumes that it is operating in the blind mode of operation and, when the screen 120 is touched without pressing down the screen 120, the exploratory mode is activated, in which the operator obtains nonvisual, for example, audio information on the virtual function element on which the hand or the finger of the operator is located. However, in another embodiment, the system can be equipped, for example, with the gaze recognition module 160 of FIG. 1, so that the gaze recognition module 160 recognizes whether the operator is viewing the screen 120 or not. If it is recognized that one is operating in the blind mode of operation, i.e., the operator is not viewing the screen 120, then, in the case of touching of the screen 120 without actuation of the switch 230, the exploratory mode occurs, while the activation of the associated function occurs only if the screen 120 is pressed down at the same time and the switch 230 is actuated. If the gaze recognition module 160 recognizes that the screen 120 is being viewed, then a function can also be triggered just by touching the function element without pressing the screen 120 down.

Figure 3:
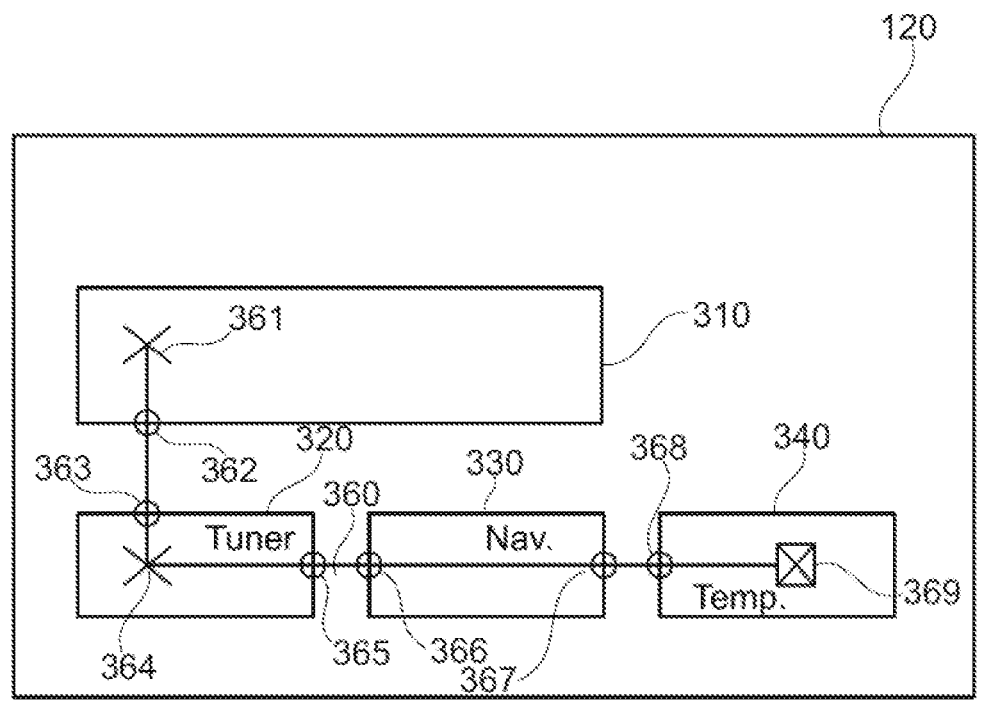
FIG. 3 diagrammatically shows the screen of the system of FIG. 1 with several different virtual function elements with the movement path of a hand of an operator over the individual virtual function elements.

The manner of functioning in the exploratory mode is explained in connection with FIG. 3. The screen 120 shows several virtual function elements 310 to 340. In an audio operating mode, the virtual function element 310 is provided, for example, to display the song that is currently being played, for example, with the name of the singer and the title of the song. For example, 360 represents the path over which a body part of the operator, for example, a finger or a hand, can be moved over the screen. In the case of the path represented, however, the operator leaves the finger on the screen 120, but the finger is not pushed towards the back, so that the switch 230 is not actuated. The operator starts his/her path on the screen 120 without looking at the screen 120, at point 361 and stays there for a certain time span, for example, for more than 2 seconds. As a result of this first predetermined actuation, the system 100 recognizes that, in the exploratory mode, an explanation should be given to the operator as to which virtual function element he/she is currently. This can occur by an audio output that the virtual function element of the media play is currently being touched, which can be a CD, DVD or another source for playing a song. In FIG. 3, the time points of the path at which the operator stays longer is represented with crosses. The operator now knows which function is stored in the virtual function element 310, since he/she has obtained this information due to prolonged positioning of the finger at point 361. When the operator then moves the finger, it is detected that the finger at point 362 leaves the area of the virtual function element, which can be indicated to the operator by vibration of the screen 120 caused by the motor. At point 363, an additional vibration occurs in which the operator is informed that he/she has landed on another virtual function element. At site 364, the operator can stay, for example, for more than 2 seconds, whereby the exploratory mode is activated again, and it is explained to the operator that the function element which has just been touched concerns the tuner. Since, due to the relative position of the virtual function elements 310 and 320, the operator knows approximately where he/she is located on the screen 120, the operator subsequently moves to the right in order to reach the virtual function element 340 where the temperature can be set. At points 365 and 366 as well as 367, a vibration occurs again when leaving the tuner element and when the function element representing the navigation function is passed through. At point 368, a vibration occurs again, so that the operator recognizes that he/she has now reached the third function element in the row. At point 369, the operator can again stay for a while, so that it is indicated to the operator that it relates here to temperature regulation. By pressing point 369, represented as a square, the associated function can be activated. Thereby, the switch 220 of FIG. 2 is activated at the same time, so that it is possible to distinguish between an exploratory mode or an actuation of the associated function. The vibration at points 362, 363, etc., can last for 50 ms, for example. If the operator knows the layout of the individual function elements with respect to one another very well, he/she can also press the screen directly at point 369 without waiting, in order to actuate the associated function. In the case of the movement from point 361 to point 369, the operator does not have to view the screen and can therefore work in the blind mode of operation.

Figure 4:
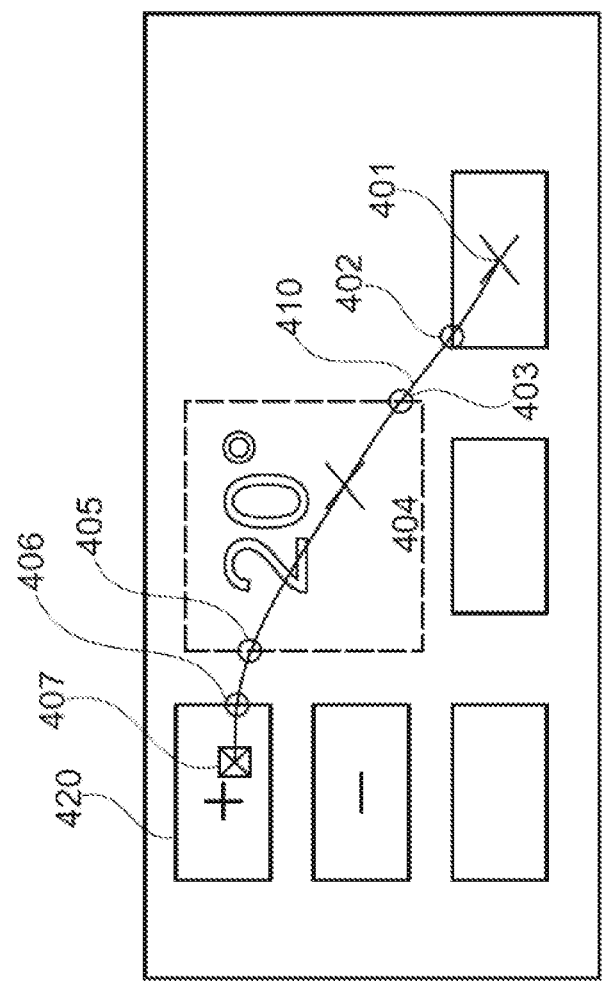
FIG. 4 shows another example of the screen with the representation of virtual function elements, showing how, in the blind mode of operation, the temperature can be changed after pressing one of the virtual function elements of FIG. 3.

In FIG. 4, it can now be seen how the screen 120 has switched to the temperature function after the pressing at point 369 of FIG. 3. The movement course is again symbolized by the movement course 410, wherein the finger starts at point 401 in its position where it lay in FIG. 3 before the associated function element was actuated. The operator can again stay there for a certain time, so that in the exploratory mode it is explained to the operator that the screen 120 for controlling the temperature has been reached. For example, the operator may be familiar with the arrangement of the individual virtual function elements on the screen 120. If the operator wishes to raise the temperature, then he/she knows that the associated virtual function element 420 is arranged at the top left. Therefore, the operator moves his/her finger on the line 410, wherein at points 402 and 403 the feedback occurs again by vibration, indicating in each case that a boundary of a virtual function element has been passed over. If the operator stays again for a while at point 404, for example, for 2 seconds, then it is communicated to the operator that the current temperature is 20° C. If the operator now wishes to raise the temperature, the finger is moved farther along the path 410 with additional vibration points 405 and 406 in the case in which the boundary of the respective function elements is passed over. If a boundary is passed over at point 406, the operator then knows that he/she has arrived at the desired function element for raising the temperature and can press this function element at point 407, so that the temperature is then raised.

As was explained in connection with FIGS. 3 and 4, the operator can activate different functions without visual contact with the screen 120.

Figure 5:
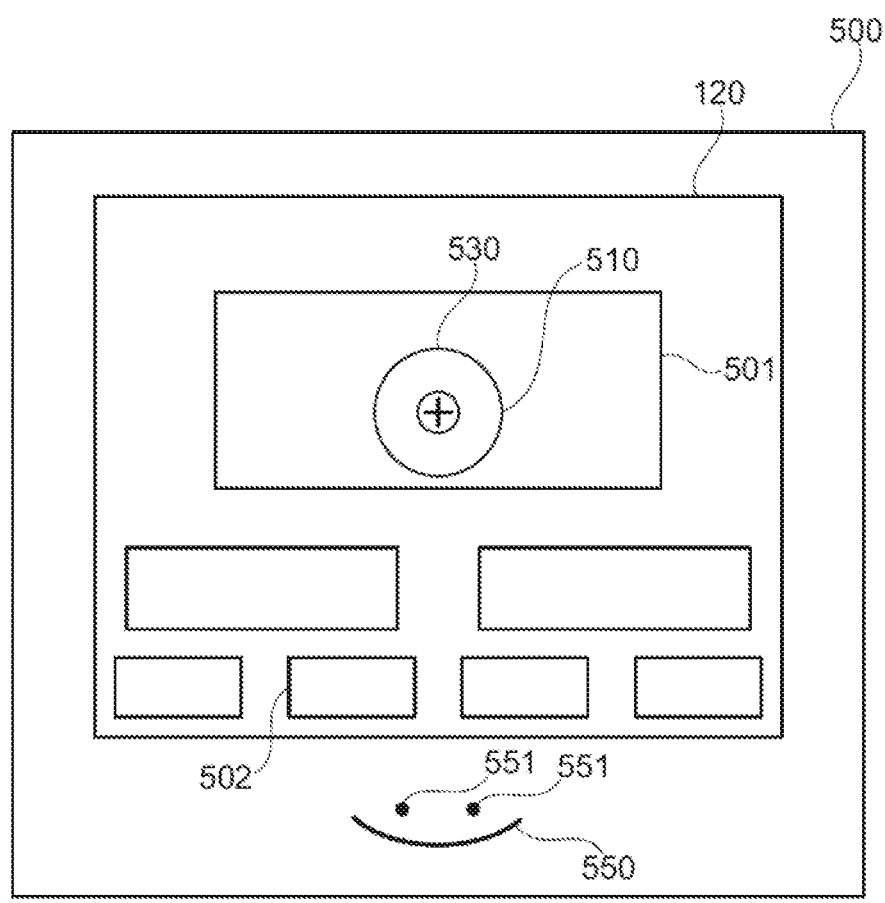
FIG. 5 shows the screen and a section of the operating system in an additional embodiment.
Figure 7:
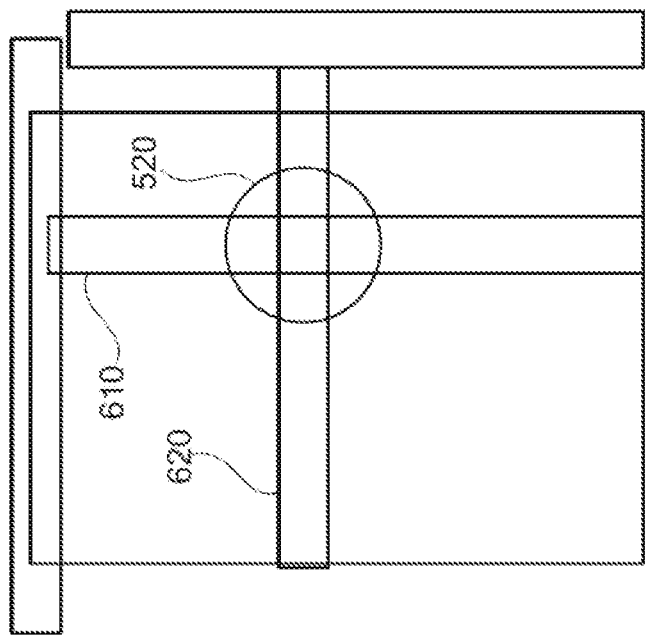
FIG. 7 shows the system of FIGS. 5 and 6 in a rear view.
Figure 6:
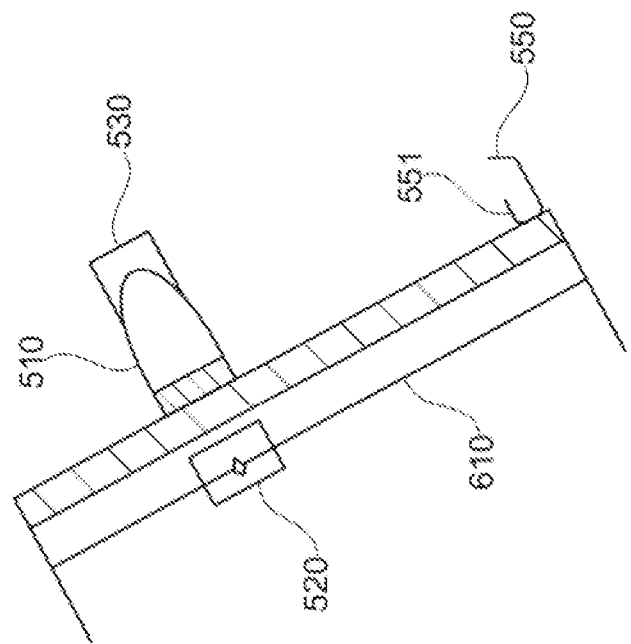
FIG. 6 shows the system of FIG. 5 in a side view.

In connection with FIGS. 5 to 7, an additional embodiment is described. In FIG. 5, the screen 120 is represented, as it lies in a frame 500. As guide element by means of which the exploratory mode can be activated, a holding element 510 is provided. As shown in FIG. 6, this holding element 510 is held on the screen 120 by a magnetic element 520 arranged on the back side of the screen. The holding element 510 can be moved on the surface of the screen 120, wherein guide rails 610 and 620 are provided, which guide the movement of the magnetic element 520 and thus of the holding element 510. The movement of the magnetic element 520 also brings about the movement of the holding element 510 on the front side of the screen 120. The holding element 510 is held on the screen by magnetic force. The holding element 510 can moreover comprise an actuation element 530 as additional operating element, in order to activate the function stored in a virtual function element if the holding element 510 comes to lie on one of the virtual function elements, such as, for example, on the virtual function element 501 of FIG. 5, and if the actuation element 530 is then pressed.

As can be seen in FIGS. 5 and 6, for the holding element 510, a parking position 550 is provided with contacts 551. The exploratory mode can thus be started in the blind mode of operation if the holding element 510 is moved out of the parking position in the direction of the screen 120. The two guide rails 610 and 620 of FIG. 7 are attached to a control in such a manner that the magnetic element 520 and thus the holding element 510 can be moved over the screen 120. For example, the control can move the two rails 610 and 620 automatically in such a manner that the magnetic element 520 comes to lie on a virtual functional element such as the function element 501. First, for example, the element 502 of FIG. 5 which is closest to the parking position is selected. The operator can indicate to the system 100 that other function elements are to be explored by moving the holding element 510. When the operator holds the holding element on a virtual function element for longer than a certain time span, for example, for 2 seconds, then the functionality of the associated function element can be explained to the operator in the exploratory mode. The explanatory mode can be started, for example, if the holding element 510 remains on a function element for a time span which is longer than the time span for starting the exploratory mode, for example, for 7 seconds. In this embodiment, the guide element 130 comprises the magnetic element 520, the guide rails 610, 620 and the holding element 510. The additional operating element for the activation of the function is implemented in the actuation element 530. If the operator wishes to activate a function, then the actuation element 530 can be pressed. In the case of the movement of the holding element 510 over the screen 120 without pressing of the actuation element, the functionality is the same as the functionality described in connection with FIGS. 3 and 4 if the switch 220 is not actuated, wherein here, for example, the holding element 510 vibrates if a virtual function element is left or if the holding element enters the area of a virtual function element. If the magnetic element 520 and the holding element 510 are located in the parking position 550, then the control unit 110 of FIG. 1 recognizes that the system is operated in the visual mode of operation. Thus, the virtual function elements represented in FIG. 5, such as the function elements 501 and 502, can be activated by direct actuation with the finger. In the blind mode of operation, this occurs with the aid of the actuation element 530. Thus, via the position of the holding element 510 relative to the parking position, a distinction is made between blind and visual mode of operation.

Figure 8:
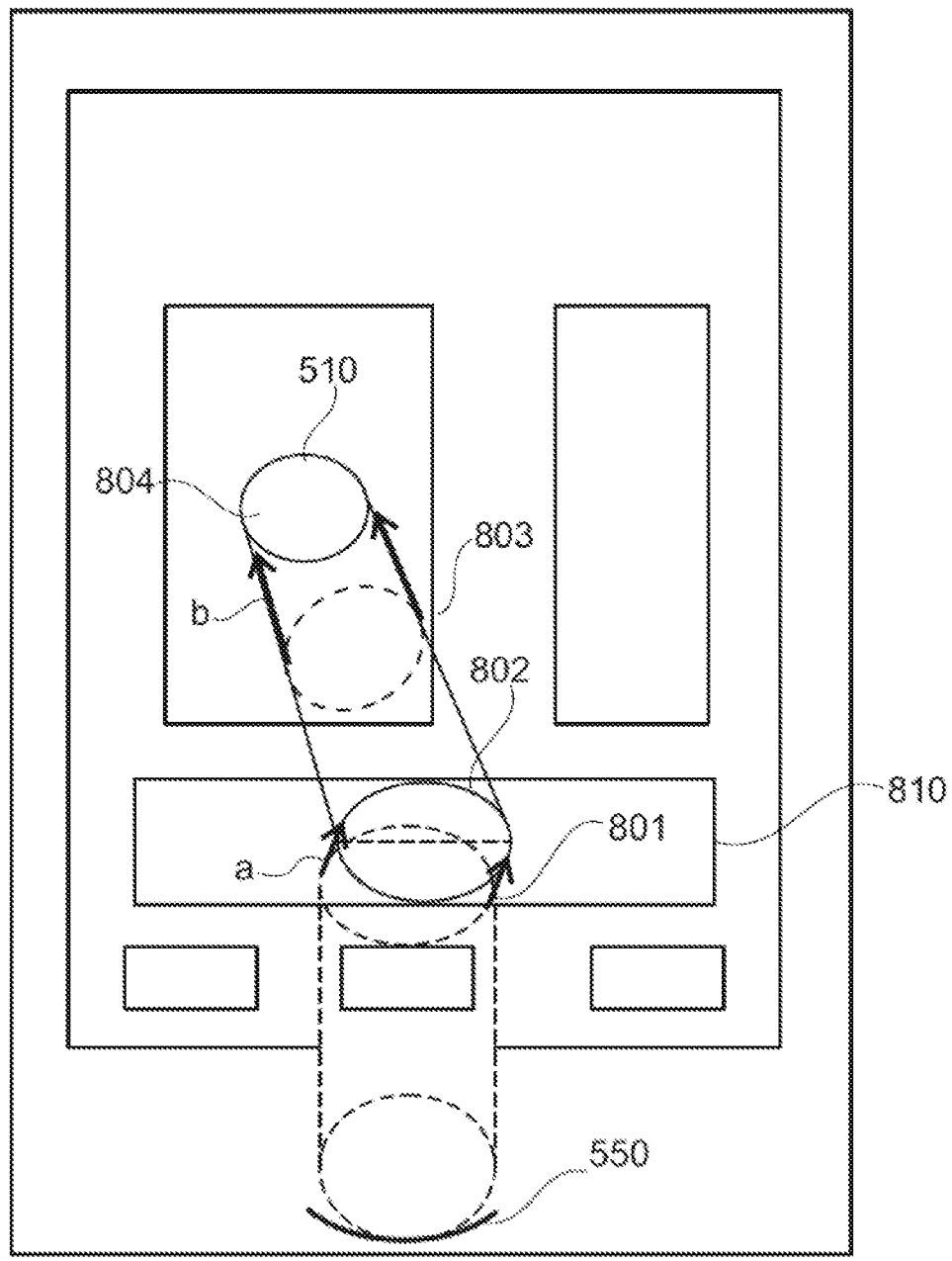
FIG. 8 shows the screen of the operating system in an additional embodiment.

In connection with FIG. 8, an additional feature of this embodiment is explained. If, in a blind mode of operation, the holding element 510 is moved out of the parking position, the system, for example, the control unit 110 with the associated processor unit, calculates the position of the holding element 510 via the position of the guide rails 610, 620. Moreover, the positions of the virtual function elements on the screen are known. The control of the holding element 510 can now occur in such a manner that, if, as shown in FIG. 8, the operator moves the holding element 510 into the broken-line position 801, a so-called snap-in function is activated, whereby the holding element 510 is centered automatically in the virtual function element 810. Thus, the holding element is moved automatically from position 801 represented with broken lines into position 802 (represented by arrow a in FIG. 8). The operator feels this centering or snap-in function and can decide whether to go along with this force and leave the guidance to the system 100 or to select his/her own path. For example, if the operator moves the holding element 510 from position 802 into position 803 which is represented with broken lines, the holding element is again centered automatically in position 804, as represented by arrows b. The holding element 510 can be moved manually and can also be controlled by the control unit 110 for the centering on the different function elements, as represented by arrows a and b.

In an additional embodiment, the system described in FIGS. 5 to 8 can comprise the voice recognition module 150 with the microphone 151. Here, the operator can say which virtual operating element he/she wishes to reach, and, if the voice recognition module 150 has recognized the voice command, the holding element 510 can then be moved to the correct position. There, for example, the associated function can then be activated by the operator by pressing the actuation element 530. In this embodiment as well, the blind mode of operation is activated if the holding element 510 is moved out of the parking position 550.

Figure 9:
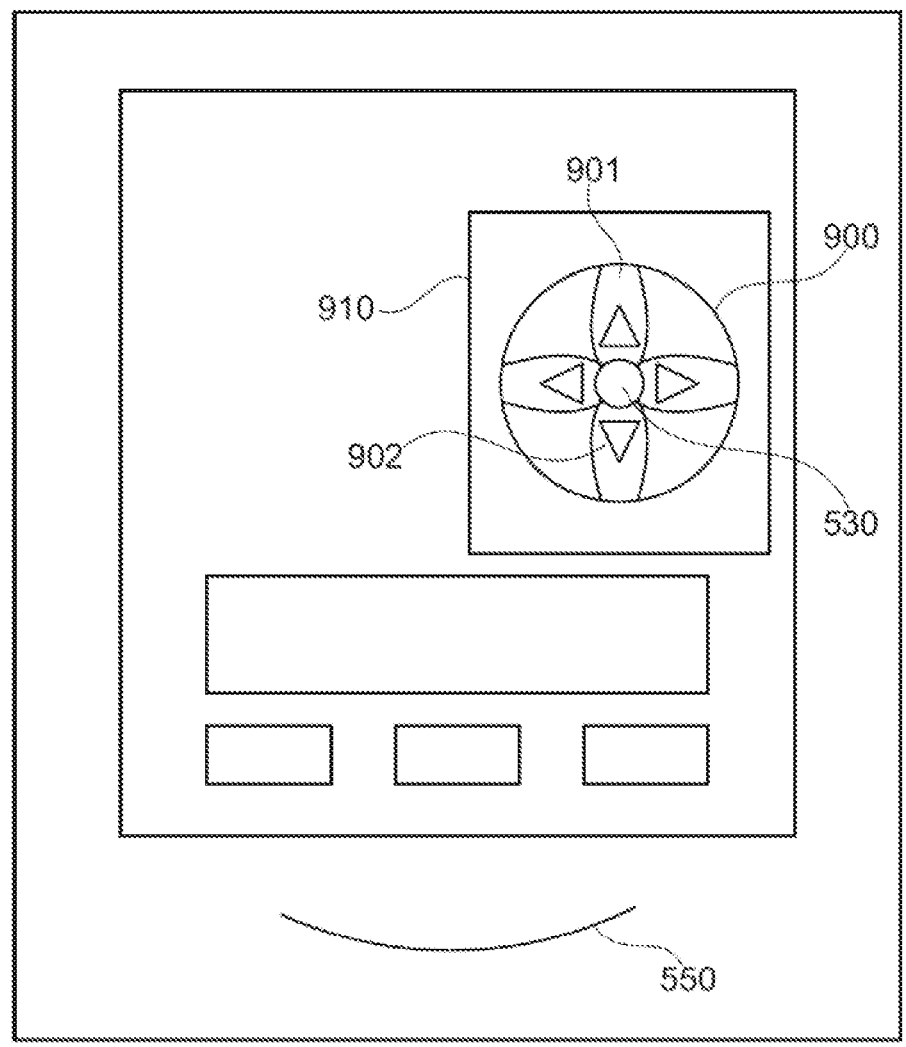
FIG. 9 shows the screen of the operating system in an additional embodiment of the operating system.
Figure 10:
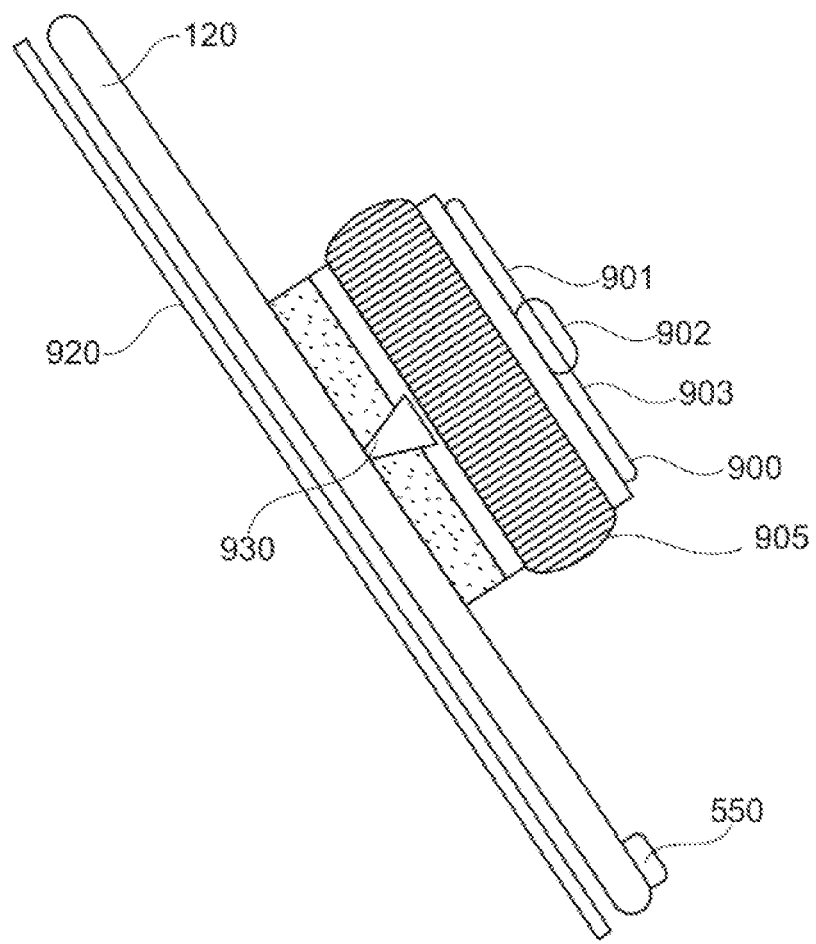
FIG. 10 shows the operating system of FIG. 9 in a side view.

In connection with FIGS. 9 and 10, an additional embodiment is described. This embodiment is similar to the embodiment described in FIGS. 5 to 8, but here a holding element 900 is freely movable and moved only by the operator. As can be seen in FIGS. 9 and 10, the holding element 900, which, for example, can comprise additional actuation elements 901 and 902, is provided. The function of the additional actuation elements 901, 902, and 903 depends on whether the holding element 900 is located in the parking position 550 or not. As represented in FIG. 10, the holding element 900 can comprise a rotatable wheel 905 which can be pressed in the direction of the screen surface. In the parking position 550, the operating elements 901 and 902, for example, can have the function of changing the sound volume or switching to the next radio station. The wheel 905 can here be used as volume control. If the holding element 900 is not in the parking position 550, then, by pressing the rotatable wheel 905 down in the direction of the screen 120, the associated function can be activated if the holding element 900 is arranged on a virtual function element such as the function element 910. The magnetic element 920 is here configured as a plate by which the holding element 900 is held on a surface of the screen 120. Moreover, an element 930 can be provided, with which the position of the holding element 900 on the screen 120 can be determined. The holding element 900 can be coupled to the vibration motor, so that the holding element vibrates if the boundary of a virtual function element has been passed over, as explained at the beginning in connection with FIGS. 2-4. The holding element 900 is moved not by the system itself, but only by the operator. In the parking position, it is again recognized that the holding element 900 is located in the parking position, and, for example, a battery, not shown, of the holding element 900 can be charged, if necessary, in the parking position. The vibration motor can here be arranged within the holding element 900. By the pressing of the rotatable wheel 905 in the direction of the surface of screen 120, the activation of a function is achieved, i.e., the rotatable wheel operates as the additional operating element, so that it can be distinguished whether a function of a virtual function element is explained to the operator or whether the function is to be activated.

In an additional embodiment, the holding element can be configured as a vehicle key. Vehicle keys are often implemented as keyless-go systems, in which the key no longer needs to be inserted in the ignition lock in order to start the vehicle. Instead, the vehicle recognizes the existence of the key in the vicinity. If this key is configured to be magnetic and inserted into the parking position 550, then the vehicle key can be configured as a holding element, and the operating system can be operated as explained above by moving the vehicle key over the screen, wherein the vehicle key comprises an additional element as actuation element, by means of which a function can be activated. Here, it is possible that operating system cannot be operated at all without the vehicle key, so that this is used at the same time as theft protection for the operating system or for the multifunction system operated thereby.

All the above-described embodiments can be used with or without the gaze recognition module 160. For example, if it is detected that the operator is not viewing the screen 120 and actuates a certain virtual function element, this can then be interpreted as the starting of the blind mode of operation. If it is recognized that the operator is not viewing the screen 120 and the surface is being touched, then an automatic transition into the exploratory mode can occur, wherein the system remains in this blind operating mode as long as the operator leaves his/her finger on the surface. Also, if the operator looks briefly at the screen 120, the system 100 does not leave the blind mode of operation. For switching between the blind mode of operation and the visual mode of operation, for example, the finger can be lifted briefly, while the eyes remain on the screen 120.

What is claimed is:

1. An operating system for operating a multifunction system, which is configured to be operated in a blind mode of operation and in a visual mode of operation, wherein the operating system comprises:
    a touch-sensitive screen configured to display a plurality of virtual function elements for controlling different functions of the multifunction system, wherein, in the blind mode of operation, the plurality of virtual function elements is actuated without viewing the touch-sensitive screen, and, in the visual mode of operation, the plurality of virtual function elements is actuated while viewing the screen,
    a guide element connected to the touch-sensitive screen;
    an additional operating element connected to the touch-sensitive screen; and
    a control unit configured to control at least the guide element and the additional operating element and to provide, in the blind mode of operation, perceivable or audible feedback in case of actuation of the touch-sensitive screen if a body part of the operator comes in contact on the touch-sensitive screen with one of the virtual function elements, wherein, if the control unit detects that the body part of the operator comes to lie on this particular virtual function element and a first predetermined actuation of this particular virtual function element by the body part is present, nonvisual information on the particular virtual function element is made available to the operator,
    wherein, in the case of actuation of the particular virtual function element, the control unit is configured to activate a function stored in the particular virtual function element with the additional operating element with a second predetermined actuation, and
    wherein the additional operating element is configured as a switch element which is arranged on a back side of the touch-sensitive screen in such a manner that the switch element is actuated if the touch-sensitive screen is shifted by the body part of the operator in a direction of the switch element, wherein the control unit is configured to activate the function stored in the particular virtual function element if the particular virtual function element on the touch-sensitive screen is touched, and the switch element is actuated by moving the touch-sensitive screen in a direction of the switch element.

2. The operating system according to claim 1, wherein the control unit is configured to distinguish whether the operating system is in the blind mode of operation or in the visual mode of operation.

3. The operating system according to claim 2, wherein, in the visual mode of operation, the control unit is configured not to enable activation of the function stored in the particular virtual function element by the operation of the additional operating element with the second predetermined actuation.

4. The operating system according to claim 3, wherein the control unit is configured to recognize, by detection of a position of the guide element relative to the touch-sensitive screen, whether the operating system is in the blind mode of operation or in the visual mode of operation.

5. The operating system according to claim 4, wherein the control unit is configured to recognize that the operating system is in the blind mode of operation if the guide element is not arranged in a predetermined parking position relative to the touch-sensitive screen.

6. The operating system according to claim 4, wherein the control unit is configured to recognize that the operating system is in the visual mode of operation if the guide element is arranged in a predetermined parking position relative to the touch-sensitive screen.

7. The operating system according to claim 1 further comprising a gaze recognition module configured to detect a gaze direction of the operator, wherein the control unit is configured to recognize that the operating system is in the blind mode of operation if the gaze recognition module recognizes that the operator is not viewing the touch-sensitive screen.

8. The operating system according to claim 1, wherein the guide element comprises a vibration element configured to initiate a vibration of the screen or of the guide element if the body part of the operator passes over an edge of a visual operating element on the touch-sensitive screen.

9. The operating system according to claim 1, wherein the guide element comprises a magnetic element which holds a holding element arranged on a side of the touch-sensitive screen facing the operator, which can be gripped by the operator and is held on the touch-sensitive screen by magnetic force by the magnetic element.

10. The operating system according to claim 9, wherein the additional operating element is configured as actuation element on the holding element, wherein the control unit is configured to activate the function stored in the particular virtual function element if the holding element lies on the particular virtual function element and the actuation element is actuated by the operator.

11. The operating system according to claim 9, wherein the magnetic element is guided on guide rails, wherein the control unit is configured to determine a position of the holding element on the screen and to move the holding element in the blind mode of operation to a closest virtual function element located on the touch-sensitive screen, wherein, if the control unit determines that the holding element is not moved, within a first time span, away from the closest virtual function element, nonvisual information on the closest virtual function element is made available to the operator.

12. The operating system according to claim 11, wherein the control unit is configured to center the holding element on the closest virtual function element if the holding element is moved in a direction of the closest virtual function element.

13. The operating system according to claim 9, wherein the holding element comprises the additional operating element in the form of a rotatable wheel which is movably mounted perpendicular to a rotation direction in a direction of the touch-sensitive screen, wherein the control unit is configured to activate the function stored in a virtual function element if the rotatable wheel is moved in the direction of the touch-sensitive screen.

14. The operating system according to claim 9, wherein the holding element comprises additional actuation elements for actuation by the operator, wherein the control unit is configured to assign functions to the additional actuation elements, which depend on whether the holding element is or is not arranged in a predetermined parking position relative to the touch-sensitive screen, wherein, in the predetermined parking position, the functions assigned to the additional actuation elements differ from the assigned functions outside of the parking position.

15. The operating system according to claim 9, wherein the holding element is configured as a key, to start an engine of a vehicle, and wherein the control unit is configured to disable the operation of the multifunction system if the key is not arranged on the touch-sensitive screen or in a predetermined parking position relative to the touch-sensitive screen.

16. The operating system according to claim 1 further comprising a voice recognition module configured to recognize a voice command of the operator and to identify a name of a virtual function element in the voice command, wherein the control unit is configured to move the guide element on the touch-sensitive screen onto the identified virtual function element.

17. The operating system according to claim 1, wherein the first predetermined actuation comprises staying of the body part on this particular virtual function element for a first predetermined time span, wherein, after this first predetermined time span, the control unit activates an exploratory mode in the blind mode of operation, in which nonvisual information is made available to the operator, as to which function is carried out if this virtual function element is activated.

18. The operating system according to claim 1, wherein after detection of a third predetermined actuation of the particular virtual function element, which differs from the first predetermined actuation and the second predetermined actuation, the control unit is configured to activate an explanatory mode in the blind mode of operation, in which explanatory mode the operator receives explanations on the function stored in this particular virtual function element.

19. An operating system for operating a multifunction system, which is configured to be operated in a blind mode of operation and in a visual mode of operation, wherein the operating system comprises:
  a touch-sensitive screen configured to display a plurality of virtual function elements for controlling different functions of the multifunction system, wherein, in the blind mode of operation, the plurality of virtual function elements is actuated without viewing the screen, and, in the visual mode of operation, the plurality of virtual function elements is actuated while viewing the screen,
  a guide element connected to the screen;
  an additional operating element connected to the screen; and
  a control unit configured to control at least the guide element and the additional operating element and to provide, in the blind mode of operation, perceivable or audible feedback in case of actuation of the screen with one of the plurality of virtual function elements, wherein, if the control unit detects a first predetermined actuation of this particular virtual function element, nonvisual information on the particular virtual function element is available to the operator,
  wherein, in the case of actuation of the particular virtual function element, the control unit is configured to activate a function stored in the particular virtual function element with the additional operating element with a second predetermined actuation, and
  wherein the guide element comprises a magnetic element which holds a holding element arranged on a side of the touch-sensitive screen facing the operator, which can be gripped by the operator and is held on the touch-sensitive screen by magnetic force by the magnetic element.

20. An operating system for operating a multifunction system, which is configured to be operated in a blind mode of operation and in a visual mode of operation, wherein the operating system comprises:
  a touch-sensitive screen configured to display a plurality of virtual function elements for controlling different functions of the multifunction system, wherein, in the blind mode of operation, the plurality of virtual function elements is actuated without viewing the touch-sensitive screen, and, in the visual mode of operation, the plurality of virtual function elements is actuated while viewing the screen,
  a guide element connected to the touch-sensitive screen;
  an additional operating element connected to the touch-sensitive screen; and
  a control unit configured to control at least the guide element and the additional operating element and to provide, in the blind mode of operation, perceivable or audible feedback in case of actuation of the touch-sensitive screen if a body part of the operator comes in contact on the touch-sensitive screen with one of the virtual function elements, wherein, if the control unit detects that the body part of the operator comes to lie on this particular virtual function element and a first predetermined actuation of this particular virtual function element by the body part is present, nonvisual information on the particular virtual function element is made available to the operator, wherein, in the case of actuation of the particular virtual function element, the control unit is configured to activate a function stored in the particular virtual function element with the additional operating element with a second predetermined actuation, wherein the control unit is configured to distinguish whether the operating system is in the blind mode of operation or in the visual mode of operation, wherein, in the visual mode of operation, the control unit is configured not to enable activation of the function stored in the particular virtual function element by the operation of the additional operating element with the second predetermined actuation.

\* \* \* \* \*